US005626849A

United States Patent [19]
Hastings et al.

[11] Patent Number: 5,626,849
[45] Date of Patent: May 6, 1997

[54] WEIGHT LOSS COMPOSITION FOR BURNING AND REDUCING SYNTHESIS OF FATS

[75] Inventors: Carl W. Hastings, Glenco; David J. Barnes, St. Louis, both of Mo.

[73] Assignee: Reliv International, Inc., Chesterfield, Mo.

[21] Appl. No.: 484,378

[22] Filed: Jun. 7, 1995

[51] Int. Cl.$^6$ .................. A61K 35/78; A61K 47/00; A61K 33/24; A61K 31/70

[52] U.S. Cl. ............... 424/195.1; 424/439; 424/655; 514/23; 514/25; 514/188; 514/557; 514/558; 514/642

[58] Field of Search .................. 424/195.1, 439, 424/655; 514/188, 557, 642, 23, 25, 558, 58

[56] References Cited

U.S. PATENT DOCUMENTS

| | | | |
|---|---|---|---|
| 4,923,855 | 5/1990 | Jensen | 514/188 |
| 4,954,492 | 9/1990 | Jensen | 514/188 |
| 5,194,615 | 3/1993 | Jensen | 546/5 |
| 5,215,750 | 6/1993 | Keane, II | 424/440 |

OTHER PUBLICATIONS

Rosenbaum, "Choosing a Chromium Supplement", The Interhealth Chromium Series: 1 (1990).

Citrimax® Product Brochure, The Interhealth Company, (1994).

Chromate® Product Brochure, The Interhealth Company (1994).

Brown, "Herbs for Health–Ginko Biloba Extract —One of the World's Best Researched Herbs" *Let's Live*, Aug. 1994.

*Primary Examiner*—John W. Rollins
*Attorney, Agent, or Firm*—Tilton, Fallon, Lungmus & Chestnut

[57] ABSTRACT

The present invention involves a dietary supplement that can be used as a weight loss composition. The composition comprises of an essentially dry mixture of chromium, L-carnitine, gamma-linolenic acid, (−) hydroxycitric acid, choline, inositol, antioxidants and herbs. The preferred antioxidants are Coenzyme Q10 and the herbs are ginkgo biloba leaves. The essentially dry mixture can be prepared as a beverage and delivered enterally. The present invention also involves a method for inducing weight loss in a mammal. The method involves administering to a mammal, preferably a human, a weight loss inducing effective amount of the above described essentially dry mixture. The weight loss inducing effective amount of the above composition is administered daily in at least two separate portions of 7.325 grams each.

20 Claims, No Drawings

WEIGHT LOSS COMPOSITION FOR BURNING AND REDUCING SYNTHESIS OF FATS

FIELD OF THE INVENTION

This invention relates to a composition that supplies chromium, L-carnitine, gamma-linolenic acid, (−) hydroxycitric acid, choline, inositol, antioxidants and herbs to the human body. The composition of this invention can be used as a dietary supplement to help facilitate weight loss. The composition can be prepared as a beverage and delivered enterally.

BACKGROUND AND SUMMARY OF THE INVENTION

At the beginning of each year, millions of Americans make a resolution that they are going to lose weight. In order to help them lose weight, many people employ the use of a over-the-counter weight loss product. For example, the below listed weight loss products are presently available:

1. Citrimax® Power (by Natures Herbs)—Provides Citrimax® which is a stabilized non-lactonized calcium salt of the free form of (−) hydroxycitric acid.
2. Energy (by Excel)—Provides 20 mg of (−) HCA, chromium, Uva Ursi, Cayenne, Ma Huang and Kola Nut.
3. Citrimax® Plus (by Natrol)—Provides 250 mg of (−) HCA, Uva Ursi, Chromium, and Cascara Sagrada.
4. Litening (by New Resolution)—Provides 125 mg of (−) HCA, chromium, yerba mate, ginseng, L-carnitine tartrate, green tea extract, hymnema sylvestre extract.
5. Smartbody (by Life Extension)—Provides an unlisted amount of (−) HCA, guarana extract, ma huang, ginger root, white willow, taurine, ascorbic acid, protease, yucca extract, amylase, bladderwrack, to-ti extract, ginkgo biloba, hawthorne berry saw palmetto, calcium borate, cellulase, chromium, lipase.
6. Citralean (by Advanced Research Products)—Provides (−) HCA, chromium, vanadyl sulfate, hymnema sylvestre.
7. Mega Fat Burner (by Proline)—Provides (−) HCA, chromium, L-carnitine.

The present invention involves a composition which is initially prepared as an essentially dry mixture that can be used as a dietary supplement to facilitate weight loss. More specifically, this composition is prepared by blending together a series of ingredients. These ingredients are: 250 to 500 mg (−) hydroxycitric acid, 50 to 125 mg L-carnitine, 25 to 100 mg chromium, 25 to 100 mg choline, 25 to 100 mg inositol 25 to 100 mg gamma-linolenic acid, 15 to 75 mg herbs and 5 to 30 mg antioxidants. The herbs are ginkgo biloba leaves and the antioxidants are preferably Coenzyme Q10. In addition to the above identified ingredients, the composition may also contain 0.15 to 0.35 g soy lecithin, 0 to 10 g carbohydrates and 0.1 to 0.5 g hydrolyzed oat flour.

The preferred composition of this invention contains 375 mg (−) hydroxycitric acid, 75 mg L-carnitine, 50 mcg chromium, 50 mg choline, 50 mg inositol, 50 mg gamma-linolenic acid, 33 mg ginkgo biloba leaves and 15 mg Coenzyme Q10. Additionally, the composition contains 0.18 g soy lecithin, 5.33 g carbohydrates and 0.33 g hydrolyzed oat flour.

The present invention also involves a method for inducing weight loss in a mammal by administering to said mammal a weight loss-inducing effective amount of the composition described above. The weight loss inducing effective amount of the composition is preferably administered at least twice a day in two separate portions of 7.325 grams each.

Once the essentially dry mixture has been blended, the composition can be delivered enterally as a beverage. The beverage is prepared by dissolving the proper amount of the essentially dry mixture in water, juice, milk or any other drinkable liquid. The recommended serving size is about 7.325 grams of the essentially dry mixture in 8 ounces of water, juice, or other ingestible liquid. As stated above, it is preferred that the recommended serving size be consumed at least twice a day.

The present composition is a dietary supplement containing several ingredients designed to help burn fat stores as well as reduce the synthesis of fats. The composition burns fat by: (1) the use of L-carnitine which transports fat from storage to be burned for energy; (2) the use of gamma linolenic acids to increase thermogenesis; (3) the use of lipotropics which serve to prevent the accumulation of fat in the liver by dissolving and mobilizing the fat stores; and (4) the use of Coenzyme Q10 which improves the efficiency of energy production at the cellular level. Furthermore, the present composition reduces synthesis of fats by: (1) the use of (−) hydroxycitric acid which inhibits the actions of ATP-citrate lyase; and (2) reducing the availability of acetyl-CoA, the building block for fatty acid and cholesterol synthesis.

DETAILED DESCRIPTION OF THE INVENTION

The present invention involves a composition for human consumption that contains chromium, L-carnitine, gamma-linolenic acid, (−) hydroxycitric acid, choline, inositol, antioxidants and herbs. This composition can be used as a dietary supplement to facilitate weight loss. More specifically, this composition is a weight-loss product that actively blocks and burns fat while curbing appetite and reducing cravings. In addition, this composition increases the rate and efficiency that the body burns fat by increasing thermogenesis (the burning and release of excess calories as heat) and provides components essential to fat burning.

The composition of this invention is initially prepared as an essentially dry mixture. This mixture is prepared by blending together the proper amounts of all the required ingredients. Once blended, the composition can be delivered enterally as a beverage. The beverage is prepared by dissolving the proper amount of the essentially dry mixture in water, juice, or any other drinkable liquid such as Reliv Ultrim® meal replacement product or Reliv Fibrestore® fiber and antioxidant supplement, by Reliv International, of Chesterfield, Mo., the assignee of the present application.

The composition of this invention can also be formulated into a lozenge by mixing the ingredients thereof into a flavored hard candy sugar base, and then subjecting this mixture to a conventional fusion or candy molding process. Additional formulations of the composition include capsules, tablets, emulsions and suspensions. Furthermore, the weight loss composition can be included in staple foods such a cakes, cookies, weight loss candy bars, etc.

In order to effectuate weight loss in a mammal such as a human, a weight loss-inducing effective amount of the essentially dry composition should be administered to said mammal. The weight loss-inducing effective amount and recommended per serving size of the composition is 7.325 grams of the essentially dry mixture. The weight loss

3 inducing effective amount of the essentially dry mixture should be consumed at least twice a day, preferably in 8 ounces of water, juice, milk or other ingestible liquid. As used herein, the term, "per serving" means 7.325 grams of the essentially dry mixture mixed with 8 ounces of an ingestible liquid.

Ingredients

The composition of the present invention includes the electrolyte chromium. Chromium is present in the formulation from about 25 to 100 mcg but preferably 50 mcg. Chromium is delivered via niacin bound chromium polynicotinate. The preferred delivery vehicle is ChromeMate®, by Interhealth Company, Concord, California. Chrome-Mate® is described in U.S. Pat. Nos., 4,923,855, 4,954,49 and 5,194,615, herewith incorporated by reference. However, other suitable niacin bound chromium polynicotinate delivery vehicles can be used.

Niacin bound chromium polynicotinate has been shown to lower blood lipid levels. Additionally, certain biologically active chromium complexes have been identified as a cofactor for insulin, such as GTF. These chromium complexes are responsible for binding insulin to cell membrane receptor sites. At these sites, insulin transports blood sugar (glucose) and vital amino acids inside the cell for energy and protein synthesis. See Rosenbaum, "Choosing A Chromium Supplement" the Interhealth Chromium Series:1 (1990).

Chromium is an important nutrient for controlling blood sugar. It helps overcome sugar cravings, a problem experienced by many overweight people due to diets high in sugars and refined carbohydrates. Chromium also helps level out the highs and lows of a high carbohydrate diet, promoting a steady stream of available glucose for continuous, prolonged energy.

Chromium also plays an important role controlling blood lipids, lowering harmful LDL cholesterol and increasing beneficial HDL cholesterol. Chromium also plays a part in the growth of muscle and the control of body fat.

The composition also contains the non-protein amino acid L-carnitine. L-carnitine present in the composition is from about 50 to 125 mg, but preferably is 75 mg. The L-Carnitine may be delivered in the form of L-Carnitine L-Tartrate, however, any other form of L-carnitine can be used.

The primary role of L-carnitine in the body is as a biocatalyst. Fats are burned for energy inside muscle cells in the cell organelle known as the mitochondria. Fats are stored in adipose cells and cannot pass through the mitochondria unless they are transported by L-carnitine. Thereupon, the amount of fat burned in the body depends on the level of L-carnitine in the muscle. The higher the level of L-carnitine in the body, the greater the amount of body fat used for fuel.

For those who do find it appropriate to diet, L-carnitine accelerates the loss of body fat without sacrificing excessive loss of lean mass. (−) Hydroxycitric Acid (HCA) has a similar effect. Studies of athletes supplementing their diet with L-carnitine showed a significant increase in the use of fat during exercise.

L-carnitine also reduces fatigue, is used in the treatment of atherosclerotic heart diseases, advantageously increases HDL cholesterol while lowering LDL cholesterol, and decreases ketone levels in the blood.

The composition also contains gamma-linoleic acid (also known as Omega). The amount of gamma-linoleic acid in the composition is from 25 to 100 mg, but preferably

4

50 mg. Gamma-linoleic acid is a polyunsaturated fatty acid which occurs as a glyceride in many seed fats. It is an essential fatty acid in the diet. The gamma-linoleic acid may be delivered in the form of Borage Oil Powder available from Traco Labs (Seymour, Illinois); however, other forms can be used.

Gamma-linoleic acid is used to facilitate weight loss by causing thermogenesis. In addition, gamma-linoleic acid appears to increase the level of brown fat Na/K ATPase activity. Brown fat readily burns fat stores for energy and the specific enzyme Na/K ATPase controls the rate of metabolism.

Furthermore, gamma-linoleic acid is known to have some important anti-inflammatory properties, is used to combat high blood pressure, lowers blood viscosity and reduces LDL cholesterol, and is known to improve immune response.

The composition also contains (−) hydroxycitric acid (referred to herein as "HCA"). The amount of (−) HCA present is from about 250 to 500 mg, but preferably 375 mg. The preferred delivery vehicle for (−) HCA is Citrimax®, available from Interhealth Company, Concord, California. Citrimax® is a stabilized non-lactonized calcium salt of the free form of (−) HCA. However, other delivery vehicles can be used.

(−) HCA reduces the conversion of carbohydrate calories into fats. It does this by inhibiting the actions of ATP-citrate lyase, the enzyme which converts citrate into fatty acids and cholesterol in the primary pathway of fat synthesis in the body. The actions of (−) HCA increase the production and storage of glycogen (which is found in the liver, small intestine and muscles of mammals) while reducing both appetite and weight gain. (−) Hydroxycitric acid also causes calories to be burned in an energy cycle similar to thermogenesis.

(−) HCA also increases the clearance of LDL cholesterol, reduces appetite, does not cross the blood-brain barrier, does not stimulate the central nervous system, does not cause insomnia, nervousness, depression, hypertension or rapid heart rate associated with most prescription and over the counter diet aids and can be combined with other nutrients to enhance benefits.

The composition also contains from about 25 to 100 mg choline and from about 25 to 100 mg inositol. It is preferred that the composition contain 50 mg of choline and 50 mg of inositol. The choline can be delivered in the form of choline bitartrate, but other forms can be used. The inositol can be delivered in any form suitable for use.

Choline and inositol are members of the vitamin B complex which are classified as lipotropics. Lipotropics serve to prevent the accumulation of fat in the liver by dissolving and mobilizing the fat stores. Lipotropics also detoxify the waste by-products of protein synthesis, increase resistance to disease by stimulating the activity of the thymus gland, increase the production of lecithin in the liver and reduce LDL cholesterol and increase HDL cholesterol.

The composition also contains antioxidants. The preferred antioxidant is coenzyme Q10 (coQ10). The amount of coenzyme Q10 present in the composition is from about 5 to 30 mg, but preferably 15 mg.

Coenzyme Q10 is also called a ubiquinone because it is present in nearly all cells of the body, is obtained from the diet, and is also produced by the body. Like L-carnitine, CoQ10 plays an important role with mitochondria. Coenzyme Q10 helps produce adenosine triphosphate (ATP), which is a chemical responsible for the storage of energy in the body. Therefore, CoQ10 is essential for virtually all energy production.

In weight loss, CoQ10 improves the efficiency of energy production at the cellular level. Coenzyme Q10 is also used to maintain immunity function and lowering blood pressure.

The composition also contains herbs. The preferred herb is ginkgo biloba leaves. The amount of ginkgo biloba leaves present in the invention is from about 15 to 75 mg, but preferably 33 mg. Ginkgo biloba leaves is known to have some antioxidant activity. More particularly, its antioxidant activity extends to the central nervous system and the eye with protective effects noted for the retina. Ginkgo biloba leaves also as act an anti depressant.

Other Ingredients

In addition to the above disclosed ingredients, the invention can also contain lecithin, flavoring agents, hydrolyzed oat flour and carbohydrates.

The composition of this invention may include a lecithin, preferably soy lecithin. The amount of soy lecithin that can be used is in the range of 0.15 to 0.35 g, but preferably in the amount of 0.18 g per serving. The soy lecithin is used as an emulsifier and processing aid to improve flow properties.

The composition can also include hydrolyzed oat flour. The amount of hydrolyzed oat flour present in the composition is in the amount 0.1 to 0.5 g, but preferably 0.33 g. The hydrolyzed oat flour can be Quaker Oatrim®(Quaker Oat Company, Chicago, Ill.), such as Oatrim® 5Q. Studies have found that individuals taking Quaker Oatrim® exhibited a substantial drop in artery-clogging LDL cholesterol without a decrease in beneficial HDL cholesterol. Additionally, their ability to process sugar from a meal improved significantly. These studies have also shown that Oatrim® is a factor in weight loss. In one study, twenty-four volunteers exhibited weight loss while taking Oatrim® despite increases in their caloric intake.

The composition can be used unflavored or can contain flavoring agents or additives. The flavoring additives can include fruit flavors, botanical flavors and mixtures thereof. As used herein, the term "fruit flavor" denotes flavors derived from natural edible reproductive prepared flavors made to stimulate fruit flavors derived from natural sources. Flavoring additives can include pineapple flavor, orange flavor, lemon flavor, lime flavor, fruit punch and mixtures thereof. Other flavors such as grape flavor, cherry flavor, apply flavor and mixtures thereof can also be used. The amount of the flavor to be used depends upon the flavor or flavors selected, the flavor impression desired, and the form of flavor added.

The composition may also include a carbohydrate source. In particular, the composition can contain the carbohydrate maltodextrin. Maltodextrin is a complex carbohydrate. The amount of maltodextrin present in the composition is in the amount of 0 to 10, but preferably, 5.33 g. Maltodextrin is used as a blending base.

EXAMPLE 1

Table 1 shows how to make a weight-loss composition within the scope of the invention. The composition is prepared by mixing the ingredients listed below to form an essentially dry mixture. To make an orally deliverable beverage composition within the scope of this invention, 7.325 grams of this blended essentially dry mixture is mixed with 8 ounces of water, juice, milk or other liquid. To effectuate weight loss, the resulting weight loss beverage is consumed at least twice a day.

TABLE 1

| Ingredient | Pounds | % |
|---|---|---|
| Citrimax® | 82.48 | 10.31 |
| Maltodextrin QD 500 | 582.75 | 72.84 |
| OATRIM 5Q | 36.16 | 4.52 |
| L-Carnitine-L-Tartrate | 13.36 | 1.67 |
| Borage Oil Powder (15% GLA) | 39.76 | 4.97 |
| Ginkgo Biloba Leaves | 3.60 | 0.45 |
| Lecithin | 20.00 | 2.50 |
| Choline Bitartrate | 13.68 | 1.71 |
| Inositol | 6.48 | 0.81 |
| Coenzyme Q10 | 1.68 | 0.21 |
| Chromate® | 0.054 | 0.0067 |
| Totals | 800.00 | 100.00 |

EXAMPLE 2

This example demonstrates the blending procedure that can be used to make the weight loss composition of the present invention.

Blending Procedure

1. Check Staged Pallets and Barrels for Correct:
   A. Quality Assurance Release
   B. Batch Numbers
   C. Paperwork
2. Arrange partial and full bag ingredients on a pallet for rapid addition to blender.
3. Turn on blender for continuous mix.
4. Add maltodextrin QD M500.
5. Gradually add liquid lecithin. Blend for eight (8) minutes.
6. Add in order while blending following ingredients:
   A. Oatrim 5Q
   B. Citrimax®
   C. Borage Oil Powder
   D. Choline Bitartrate
   E. Inositol
   F. Coenzyme Q 10
   G. L-Carnitine L-Tartrate
   H. ChromeMate®*
   I. Ginkgo Biloba Leaves* * Mix With partial of Citrimax®
7. Blend eight (8) minutes.
8. Upon blending completion, test and sample.

Although the invention has been described primarily in connection with special and preferred embodiments, it will be understood that it is capable of modification without departing from the scope of the invention. The following claims are intended to cover all variations, uses, or adaptations of the invention, following, in general, the principles thereof and including such departures from the present disclosure as come within known or customary practice in the field to which the invention pertains, or as are obvious to persons skilled in the field.

We claim:

1. A weight loss composition comprising:
   250 to 500 mg (−) hydroxycitric acid;
   50 to 125 mg L-carnitine;
   25 to 100 mcg Chromium;
   25 to 100 mg Choline;

25 to 100 mg Inositol;

25 to 100 mg Gamma-Linolenic Acid;

15 to 75 mg herbs; and 5 to 30 mg antioxidants.

2. The composition of claim 1 wherein the herbs are ginkgo biloba leaves and the antioxidants are Coenzyme Q10.

3. The composition of claims 1 or 2 further comprising 0.15 to 0.35 g soy lecithin, 0 to 10 g carbohydrates, and 0.1 to 0.5 g oat flour.

4. The composition of claim 3 where the carbohydrates are maltodextrin and the oat flour is hydrolyzed.

5. A weight loss composition comprising:

250 to 500 mg (−) hydroxycitric acid;

50 to 125 mg L-carnitine;

25 to 100 mcg Chromium;

25 to 100 mg Choline;

25 to 100 mg Inositol;

25 to 100 mg Gamma-Linolenic Acid;

15 to 75 mg Ginkgo Biloba Leaves; and 5 to 30 mg Coenzyme Q10.

6. The composition of claim 5 further comprising 0.15 to 0.35 soy lecithin, 0 to 10 g carbohydrates, and 0.1 to 0.5 g oat flour.

7. The composition of claim 6 where the carbohydrates are maltodextrin and the oat flour is hydrolyzed.

8. A weight loss composition comprising:

375 mg (−) hydroxycitric acid;

75 mg L-Carnitine;

50 mcg Chromium;

50 mg Choline;

50 mg Inositol;

501 mg Gamma-Linolenic Acid;

b 33mg Ginkgo Biloba Leaves; and 15 mg Coenzyme Q10.

9. The composition of claim 8 further comprising 0.18 g soy lecithin, 5.3 g carbohydrates, and 0.33 g oat flour.

10. An aqueous beverage composition to facilitate weight loss comprising:

250 to 500 mg (−) hydroxycitric acid;

50 to 125 mg L-carnitine;

25 to 100 mcg Chromium;

25 to 100 mg Choline;

25 to 100 mg Inositol;

25 to 100 mg Gamma-Linolenic Acid;

15 to 75 mg Ginkgo Biloba Leaves; and 5 to 30 mg Coenzyme Q10.

11. The aqueous beverage composition of claim 10 further comprising 0.15 to 0.35 g soy lecithin, 0 to 10 g carbohydrates, and 0.1 to 0.5 g oat flour.

12. The aqueous beverage composition of claim 11 wherein the carbohydrates are maltodextrin and the oat flour is hydrolyzed.

13. A method of inducing weight loss in a mammal, comprising administering to said mammal a weight loss inducing effective amount of the composition of claim 1.

14. The amount of claim 13 wherein the weight loss inducing effective amount is administered at least daily in two separate portions of 7.325 grams each.

15. A method of inducing weight loss in a mammal, comprising administering to said mammal a weight loss inducing effective amount of the composition of claim 5.

16. The method of claim 15 wherein the weight loss inducing effective amount is administered daily in two separate portions of 7.325 grams each.

17. A method of inducing weight loss in a mammal, comprising administering to said mammal a weight loss inducing effective amount of the composition of claim 8.

18. The method of claim 17 wherein the weight loss inducing effective amount is administered at least daily in two separate portions of 7.325 grams each.

19. A method of inducing weight loss in a mammal, comprising administering to said mammal a weight loss inducing effective amount of the composition of claim 10.

20. The method of claim 19 wherein the weight loss inducing effective amount is administered daily in at least two separate portions of 7.325 grams each.

* * * * *

UNITED STATES PATENT AND TRADEMARK OFFICE
CERTIFICATE OF CORRECTION

PATENT NO. : 5,626,849

DATED : May 6, 1997

INVENTOR(S) : Carl W. Hastings et al

It is certified that error appears in the above-identified patent and that said Letters Patent is hereby corrected as shown below:

Claim 8, Col. 7, Line 36, "501 mg Gamma-Linolenic Acid;" should be ---50 mg Gamma-Linolenic Acid;---

Claim 8, Col. 7, Line 37, "b 33 mg Ginkgo Biloba Leaves; and should be ---33 mg Ginkgo Biloba Leaves; and---

Claim 14, Col. 8, Line 21, "administered at least daily in" should be ---administered daily in at least---

Claim 16, Col. 8, Line 27, "administered daily in" should be ---administered daily in at least---

Claim 18, Col. 8, Line 34, "administered at least daily in" should be ---administered daily in at least---

Signed and Sealed this

Nineteenth Day of August, 1997

Attest:

BRUCE LEHMAN

Attesting Officer

Commissioner of Patents and Trademarks